(12) United States Patent
Jakoby

(10) Patent No.: US 6,776,024 B2
(45) Date of Patent: Aug. 17, 2004

(54) METHOD OF EVALUATING THE WEAR OF ENGINE OIL TAKING INTO ACCOUNT THE ADDITION OF FRESH OIL

(75) Inventor: Bernhard Jakoby, Vienna (AT)

(73) Assignee: Robert Bosch GmbH, Stuttgart (DE)

( * ) Notice: Subject to any disclaimer, the term of this patent is extended or adjusted under 35 U.S.C. 154(b) by 13 days.

(21) Appl. No.: 10/221,091

(22) PCT Filed: Feb. 15, 2001

(86) PCT No.: PCT/DE01/00563

§ 371 (c)(1),
(2), (4) Date: Dec. 6, 2002

(87) PCT Pub. No.: WO01/67096

PCT Pub. Date: Sep. 13, 2001

(65) Prior Publication Data

US 2003/0172722 A1 Sep. 18, 2003

(30) Foreign Application Priority Data

Mar. 7, 2000 (DE) .......................... 100 10 976

(51) Int. Cl.⁷ .......................... G01N 33/26; G01N 11/00
(52) U.S. Cl. .......................... 73/10; 73/53.05; 73/54.01; 73/54.02; 702/50
(58) Field of Search ...................... 73/10, 53.05, 54.01, 73/54.02; 702/50

(56) References Cited

U.S. PATENT DOCUMENTS

| | | | |
|---|---|---|---|
| 4,943,797 A | * 7/1990 | Steffenhagen | 340/450.3 |
| 5,592,395 A | * 1/1997 | Braun et al. | 702/50 |
| 5,750,887 A | 5/1998 | Schricker | |
| 5,806,472 A | * 9/1998 | Nelson et al. | 123/73 AD |
| 5,817,928 A | 10/1998 | Garvey, III et al. | |
| 5,964,318 A | * 10/1999 | Boyle et al. | 184/1.5 |
| 6,023,961 A | 2/2000 | Feke et al. | |
| 6,151,956 A | * 11/2000 | Takahashi et al. | 73/53.05 |
| 6,449,538 B1 | * 9/2002 | Kubo et al. | 701/30 |

* cited by examiner

*Primary Examiner*—Edward Lefkowitz
*Assistant Examiner*—Michael Cygan
(74) *Attorney, Agent, or Firm*—Kenyon & Kenyon

(57) ABSTRACT

A method of evaluating engine oil wear on the basis of viscosity measurement, accounting for the addition of fresh oil. Using an oil viscosity sensor, an amount of fresh oil added is detected, then the oil viscosity sensor determines a viscosity of the oil mixture of the engine oil and fresh oil. A quantity of fresh oil added is determined in the electronic analyzer from a difference between the old oil level, i.e., the oil volume, and the new oil level. The viscosity of the fresh oil is determined from the viscosity of the old engine oil immediately before the point in time of the addition of fresh oil and from the viscosity after the addition. A hypothetical initial viscosity is calculated as a new corrected reference value from the known value of the viscosity of the old engine oil in the new condition, the quantity of the engine oil still present at the point in time of the addition, the calculated viscosity of the fresh oil and the calculated quantity of the fresh oil.

13 Claims, 1 Drawing Sheet

METHOD OF EVALUATING THE WEAR OF ENGINE OIL TAKING INTO ACCOUNT THE ADDITION OF FRESH OIL

FIELD OF THE INVENTION

The present invention relates to a method of evaluating wear in engine oil, taking into account the addition of fresh oil.

BACKGROUND INFORMATION

To aid a driver, some software-based systems display information that it is time to change the engine oil in a motor vehicle, wherein the systems are based on algorithms which analyze parameters such as the distance traveled since the last oil change or the frequency of cold starts. Other methods rely on sensor signals which directly describe the physical condition of the oil, e.g., the dielectric constant of the oil or, as a much more reliable variable, the viscosity ($\eta$) of the oil. A viscosity-based oil change criterion is derived from recording a change in viscosity since the last engine oil change, because wear on engine oil is usually associated with an increase in viscosity. For example, in one case, a viscosity value ($\eta_{max}$) may be defined as a limit value which must not exceed the viscosity value ($\eta_0$) of the fresh oil as a reference value by more than a certain percentage, e.g., no more than 30%. The viscosity threshold above which engine oil should be changed and which is displayed for the driver of the vehicle is then given by the following equation, for example:

$$\eta_{max} = k \times \eta_0 \qquad (1)$$

Factor k defines the allowed increase in viscosity, which corresponds to k=1.3 with a 30% allowed increase.

Adding fresh oil of a different type or a different viscosity class is problematical with these methods and similar methods of evaluating engine oil wear on the basis of viscosity measurements. Added oil has a different fresh oil viscosity, so the oil change criterion is subject to distortion. For example, the addition of engine oil of a higher viscosity class would simulate aging, although a de facto improvement in oil condition has been achieved by this addition of oil. Conversely, the addition of a lower-viscosity engine oil would simulate an improvement in the condition of the oil to an extent which does not conform to the actual condition. The fresh oil viscosity values for engine oil from adjacent viscosity classes typically differ by 30%.

SUMMARY OF THE INVENTION

The method according to the present invention allows evaluation of engine oil wear based on viscosity measurements, accounting for the addition of fresh oil, thereby permitting a correction of the reference value.

Specifically, the amount of oil added in topping off with fresh oil is detected by the oil level sensor, then the viscosity of the oil mixture ($\eta_2$) of engine oil and fresh oil is determined by the oil viscosity sensor after an operating time and/or after reaching a predetermined oil temperature. The quantity ($V_n$) of the added fresh oil is determined by the electronic analyzer from a difference between the old oil level, i.e., oil volume ($V_1$) and the new oil level, i.e., oil volume ($V_2$). The viscosity ($\eta_n$) of the fresh oil is determined from the viscosity ($\eta_1$) of the old engine oil immediately before the point in time of adding more oil and from the viscosity ($\eta_2$) after the addition. A hypothetical initial viscosity ($\eta'_0$) is calculated as a new corrected reference value from the known value of the viscosity ($\eta_0$) of the old engine oil in the new condition, the quantity ($V_1$) of the engine oil still present at the point in time of adding the new oil, the calculated viscosity ($\eta_n$) of the fresh oil and the calculated quantity ($V_n$) of the fresh oil. A new limit value ($\eta'_{max}$) for the viscosity threshold of the oil mixture is calculated from the corrected reference value, so that the oil should be changed after this limit value, which replaces the original value from (1), e.g., through the following computation rule:

$$\eta'_{max} = k \times \eta'_0 \qquad (2)$$

To determine the viscosity ($\eta$) of the added fresh oil and to determine the hypothetical initial viscosity ($\eta'_0$) as a new corrected reference value, a mixing rule is used, where the value sought is a function of the known viscosities and the different oil quantities.

According to another exemplary embodiment of this method, additional parameters for the aging of oil may be accounted for as a viscosity threshold by the connected electronic analyzer in determination of the limit value of the maximum allowed viscosity ($\eta'_{max}$), e.g., the temperature gradient of heating of the oil, the number of cold starts or the length of trips traveled, and/or the operating times.

The determination of the corrected reference value ($\eta'_0$) may be made more accurate by accounting for additional relationships and evaluation criteria and may even be stored as a reference characteristic in the electronic analyzer. For example, the temperature dependence of the viscosity may also be taken into account in the evaluation criteria.

To increase the accuracy of the reference value, additional evaluation methods may also be accounted for in evaluating engine oil wear, so that the engine oil quality of a vehicle may never fall below a required level without drawing the attention of the driver to an urgent need for an engine oil change.

DETAILED DESCRIPTION

Figure 1:
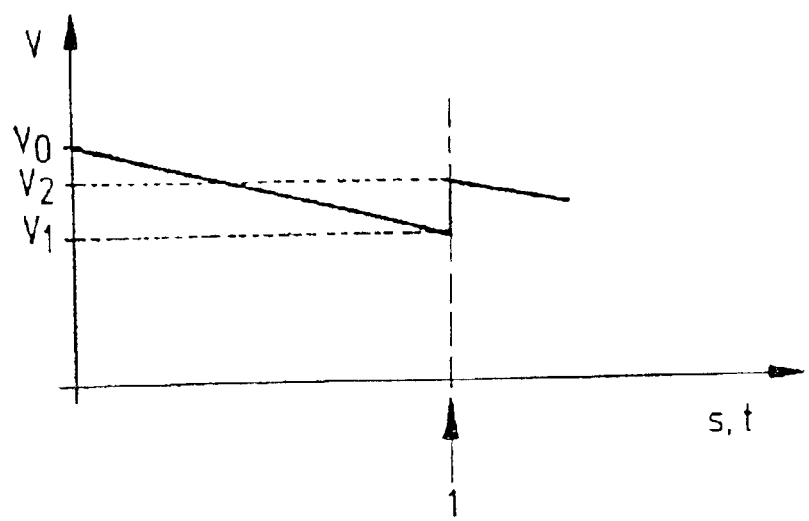
FIG. 1 illustrates a coordinate system representing a decrease in the oil volume over the operating time or the distance traveled by a motor vehicle.

FIG. 1 illustrates the typical change in oil volume ($V_0$) from a point in time of a last oil change until a point in time (1) of an addition of fresh oil ($V_1$), after which the oil volume increases again to a level ($V_2$), the various quantities, i.e., oil volumes, being determined as a function of the filling level via the level sensor and the electronic analyzer.

Figure 2:
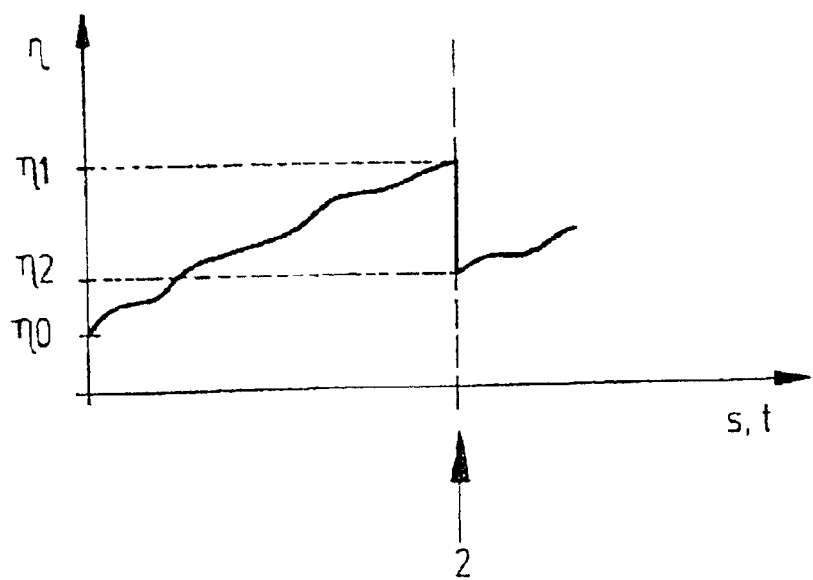
FIG. 2 illustrates a coordinate system showing a typical increase in viscosity over the operating time of an engine or distance traveled.

FIG. 2, in contrast, illustrates the increase in viscosity of an engine oil starting from a viscosity ($\eta_0$), when the engine oil is new, up to a viscosity ($\eta_2$) at a point in time (2) when oil is added. The addition of fresh oil then results in a sudden change in the value of the viscosity ($\eta_2$) which characterizes the mixture of oil which is already partially "used" and freshly added oil. For the illustration in FIG. 2, it has been assumed that the resulting viscosity value ($\eta_2$) drops when fresh oil is added, although that need not necessarily be the case if engine oil of a higher viscosity class than the oil used in the last oil change is added. The viscosity value ($\eta_2$) is not determined immediately after the addition of oil because of incomplete mixing, but instead is established as a steady-state measured value only after a certain engine operating time and after thorough mixing of the engine oils to form a homogeneous mixture.

The quantity of fresh oil ($V_n$) added is determined from the measured oil level, i.e., the volume derived therefrom:

$$V_n = V_2 - V_1.$$

A mixing rule is used to determine the viscosity ($\eta_n$) of the engine oil added, which is not known a priori. Such mixing rules are formulated on the basis of scientific models for the respective materials in question, and they describe the resulting viscosity for a mixture of two fluids. In general, the viscosity of the mixture of the fresh oil added and the oil already present is obtained as a function of the viscosity ($\eta_1$) of the oil already present, its volume fraction ($V_1$), the viscosity ($\eta_n$) of the fresh oil added and its volume ($V_n$). A model for such a mixing rule is based on the assumption that the viscosities of the mixed oils are weighted with the corresponding relative volume fractions:

$$\eta_2 = \eta_1(V_1/(V_1+V_n)) + \eta_n(V_n/(V_1+V_n))$$

By rearranging, the viscosity ($\eta_n$) of the added fresh oil may be calculated from the known variables $V_1$, $\eta_1$, $V_n$ and $\eta_2$. Using the mixing rule again, the hypothetical viscosity ($\eta'_0$) is determined which would be obtained by mixing the quantity ($V_n$) of fresh oil added with the last oil change having the viscosity ($\eta_0$) and the quantity ($V_n$) of fresh oil of the viscosity ($\eta_n$) added. New limit value $\eta'_{max}$ is determined from this new corrected reference value, e.g., by calculating it by multiplying by factor k for the oil mixture, which then replaces the original value (1).

The absolute limit value for the acceptability of a viscosity, however, may also be formulated more generally as a function in which the initial viscosity ($\eta_0$) of the fresh oil or the calculated hypothetical initial viscosity ($\eta'_0$) of the oil mixture is accounted for in addition to other parameters for the oil change recommendation. The change in viscosity in comparison with the reference value will in the general case enter into a more complex algorithm which takes into account other characteristic values.

The method of evaluating engine oil wear on the basis of viscosity measurements, accounting for an addition of fresh oil, is thus performed by characterizing the oil mixture by using a limit value representing the fresh oil. In the addition of oil, a new corrected reference value for the resulting oil mixture is determined from the quantity of oil added and the resulting mixture viscosity, accounting for the partial wear of the oil already present in the engine. The reference value may also be a reference characteristic, e.g., if the temperature dependence of the viscosity is also taken into account. The viscosity-based evaluation of wear may also be just one of several aspects of a more general evaluation algorithm for evaluating the condition of the engine oil.

What is claimed is:

1. A method of evaluating wear in engine oil based on viscosity measurements, accounting for an addition of fresh oil to aged engine oil using an oil viscosity sensor, an oil level sensor and a connected electronic analyzer having a display device, and determining an aging of the aged engine oil and determining an oil change interval recommendation resulting therefrom as a reference value by evaluating a change in a prevailing oil viscosity at at least one temperature, in comparison with a viscosity of the fresh oil added at a last oil change, the method comprising:

detecting a quantity of oil used in the addition of the fresh oil using the oil level sensor;

determining a viscosity of an oil mixture of the aged engine oil and the fresh oil together with a temperature using the oil viscosity sensor at at least one temperature;

determining the quantity of the fresh oil added, using the electronic analyzer, from a difference between one of an old oil level and oil volume, and one of a new oil level and oil volume;

determining a viscosity of the fresh oil from a viscosity of the aged engine oil immediately before and immediately after the addition of the fresh oil; and calculating a hypothetical initial viscosity as a new corrected reference value from an initial viscosity of the aged engine oil when new, the oil volume still present at a point in time of the addition, a determined viscosity of the fresh oil, and a determined quantity of fresh oil.

2. The method of claim 1, further comprising:

determining a viscosity limit value from the viscosity of the aged engine oil when new by multiplying the initial viscosity by a factor of an admissible increase in viscosity, so that a display of an end of an oil change interval by the display device is triggered when the viscosity limit value is exceeded by the viscosity of the oil mixture measured at a given time at a corresponding temperature value; and obtaining a new limit value from the hypothetical initial viscosity, when adding fresh oil, by multiplying the initial viscosity by the factor.

3. The method of claim 2, wherein the factor has a value greater than 1.

4. The method of claim 2, wherein a mixing rule is used to determine at least one of the calculated viscosity of the fresh oil and the hypothetical initial viscosity of the oil mixture when new as the new corrected reference value.

5. The method of claim 2, wherein at least one indirect influencing factor on the aging of the engine oil is accounted for in the determining the oil change interval.

6. The method of claim 5, wherein the at least one indirect influencing factor includes an oil heating temperature gradient.

7. The method of claim 5, wherein the at least one indirect influencing factor includes at least one of the number of kilometers driven and the number of hours of operation since the last oil change.

8. The method of claim 5, wherein the at least one indirect influencing factor includes at least one of a rotational speed of the engine and an oil temperature characteristic.

9. The method of claim 5, wherein the at least one indirect influencing factor includes a dielectric constant of the engine oil.

10. The method of claim 5, wherein the at least one indirect influencing factor includes a conductivity of the engine oil.

11. The method of in claim 5, wherein the at least one indirect influencing factor includes one of a frequency of cold starts and a load on the vehicle.

12. The method of claim 1, wherein the new corrected reference value is formed by accounting for an additional measured relationship as a reference characteristic.

13. The method of claim 12, wherein the reference characteristic includes a viscosity/temperature characteristic, wherein unmeasured ranges are supplemented by at least one of interpolation and extrapolation.

* * * * *